(12) United States Patent
Steger

(10) Patent No.: US 10,213,841 B2
(45) Date of Patent: Feb. 26, 2019

(54) HOLDING APPARATUS FOR A DENTAL WORKPIECE

(71) Applicant: Heinrich Steger, Bruneck (IT)

(72) Inventor: Heinrich Steger, Bruneck (IT)

( * ) Notice: Subject to any disclaimer, the term of this patent is extended or adjusted under 35 U.S.C. 154(b) by 120 days.

(21) Appl. No.: 15/001,679

(22) Filed: Jan. 20, 2016

(65) Prior Publication Data

US 2016/0206410 A1    Jul. 21, 2016

(30) Foreign Application Priority Data

Jan. 21, 2015    (AT) .................... A 25/2015

(51) Int. Cl.
*B23Q 3/06* (2006.01)
*B23B 31/20* (2006.01)
*A61C 13/00* (2006.01)

(52) U.S. Cl.
CPC .......... *B23B 31/20* (2013.01); *A61C 13/0006* (2013.01); *A61C 13/0022* (2013.01); *B23Q 3/062* (2013.01)

(58) Field of Classification Search
CPC ............ B23C 2226/18; A61C 13/0004; A61C 13/0006; A61C 13/0022; B23B 31/20; B23B 31/201; Y10T 279/17495; Y10T 279/17504; Y10T 279/17512; Y10T 279/17521; Y10T 279/17529; Y10T 279/17538; Y10T 279/17547; Y10T 279/17247; Y10T 279/17299; Y10T 279/17307; Y10T 279/17316; Y10T 279/17324; Y10T 279/17333; Y10T 279/17341; Y10T 279/17351; Y10T 279/17411; Y10T 279/17418; Y10T 279/17427; Y10T 279/17435;
(Continued)

(56) References Cited

U.S. PATENT DOCUMENTS

| 2,400,314 A | * | 5/1946 | Obecny | ................ | B23Q 3/061 |
| | | | | | 269/153 |
| 2,869,433 A | * | 1/1959 | Dery | ..................... | B23Q 3/061 |
| | | | | | 269/154 |

(Continued)

FOREIGN PATENT DOCUMENTS

| DE | 41 37 563 | 5/1993 |
| DE | 94 07 491 | 4/1995 |

(Continued)

OTHER PUBLICATIONS

KR 10-1419832 Machine Translation, pp. 7-16, Nov. 7, 2017.*
(Continued)

*Primary Examiner* — Nicole N Ramos
(74) *Attorney, Agent, or Firm* — Wenderoth, Lind & Ponack, L.L.P.

(57) ABSTRACT

A holding apparatus for an in particular dental workpiece includes a holding element and a fixing device. The workpiece can be fixed to the holding apparatus by a relative movement of the fixing device with respect to the holding element. The fixing device or the holding element has a split sleeve, and the inside surface of the split sleeve forms a clamping surface for the workpiece. Upon the relative movement of the fixing device with respect to the holding element, the workpiece can be braced against the holding device by the clamping surface.

13 Claims, 11 Drawing Sheets

(58) Field of Classification Search
CPC .. Y10T 279/17444; Y10T 409/308904; B23Q 3/062
See application file for complete search history.

(56) References Cited

U.S. PATENT DOCUMENTS

| | | | | |
|---|---|---|---|---|
| 3,698,060 | A | * | 10/1972 | Helton .................... F01L 1/146 269/287 |
| 3,861,867 | A | * | 1/1975 | Ouhl ...................... A61C 13/12 206/562 |
| 4,103,589 | A | * | 8/1978 | Francis ................. B23B 31/204 279/4.08 |
| 4,643,409 | A | * | 2/1987 | Hamatani ............... B25B 11/00 269/152 |
| 2002/0137002 | A1 | | 9/2002 | Bodenmiller |
| 2003/0132539 | A1 | | 7/2003 | Althoff |
| 2009/0274994 | A1 | | 11/2009 | Jung et al. |
| 2013/0157222 | A1 | * | 6/2013 | Yeom ................... B23Q 1/5406 433/172 |

FOREIGN PATENT DOCUMENTS

| | | |
|---|---|---|
| DE | 44 36 231 | 11/1995 |
| DE | 100 37 531 | 1/2002 |
| DE | 201 05 248 | 9/2002 |
| DE | 20 2010 001 125 | 5/2010 |
| DE | 10 2010 061 116 | 6/2012 |
| EP | 1 068 839 | 1/2001 |
| EP | 2 026 931 | 2/2009 |
| EP | 2 604 219 | 6/2013 |
| EP | 2 837 357 | 2/2015 |
| KR | 10-1419832 | 7/2014 |
| WO | 95/30382 | 11/1995 |
| WO | 2007/143765 | 12/2007 |
| WO | 2013/117540 | 8/2013 |

OTHER PUBLICATIONS

European Search Report dated May 20, 2016 in European Application No. 16 15 2024, with English translation.
Austrian Search Report dated Jun. 17, 2015 in corresponding Austrian Patent Application No. 25/2015 (with English translation).

* cited by examiner

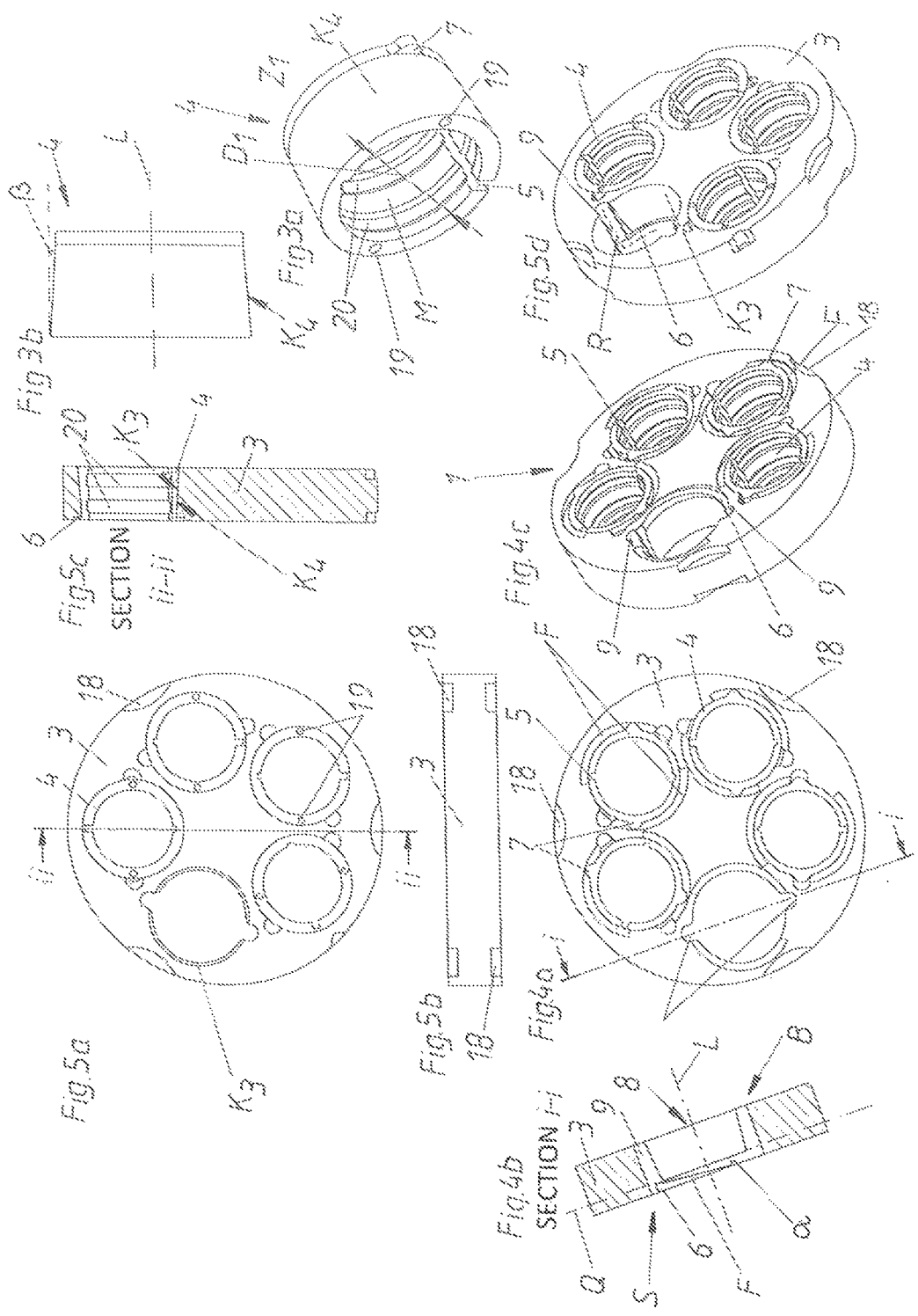

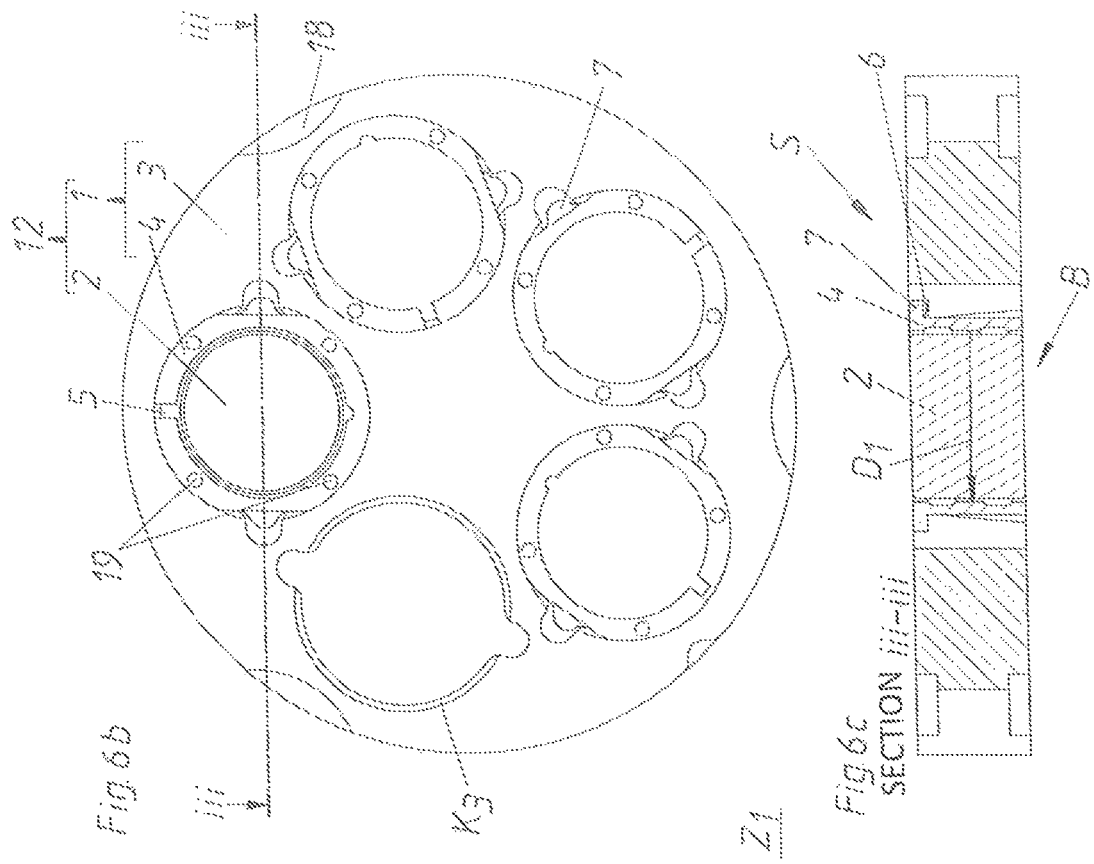
Fig.6b
Fig.6c
SECTION III-III
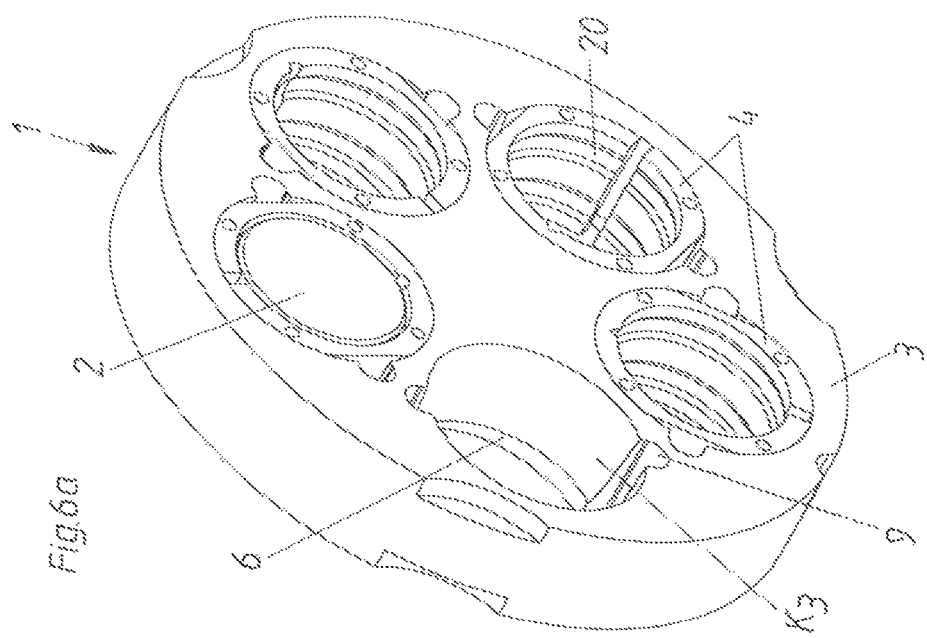
Fig.6a

SECTION iv–iv

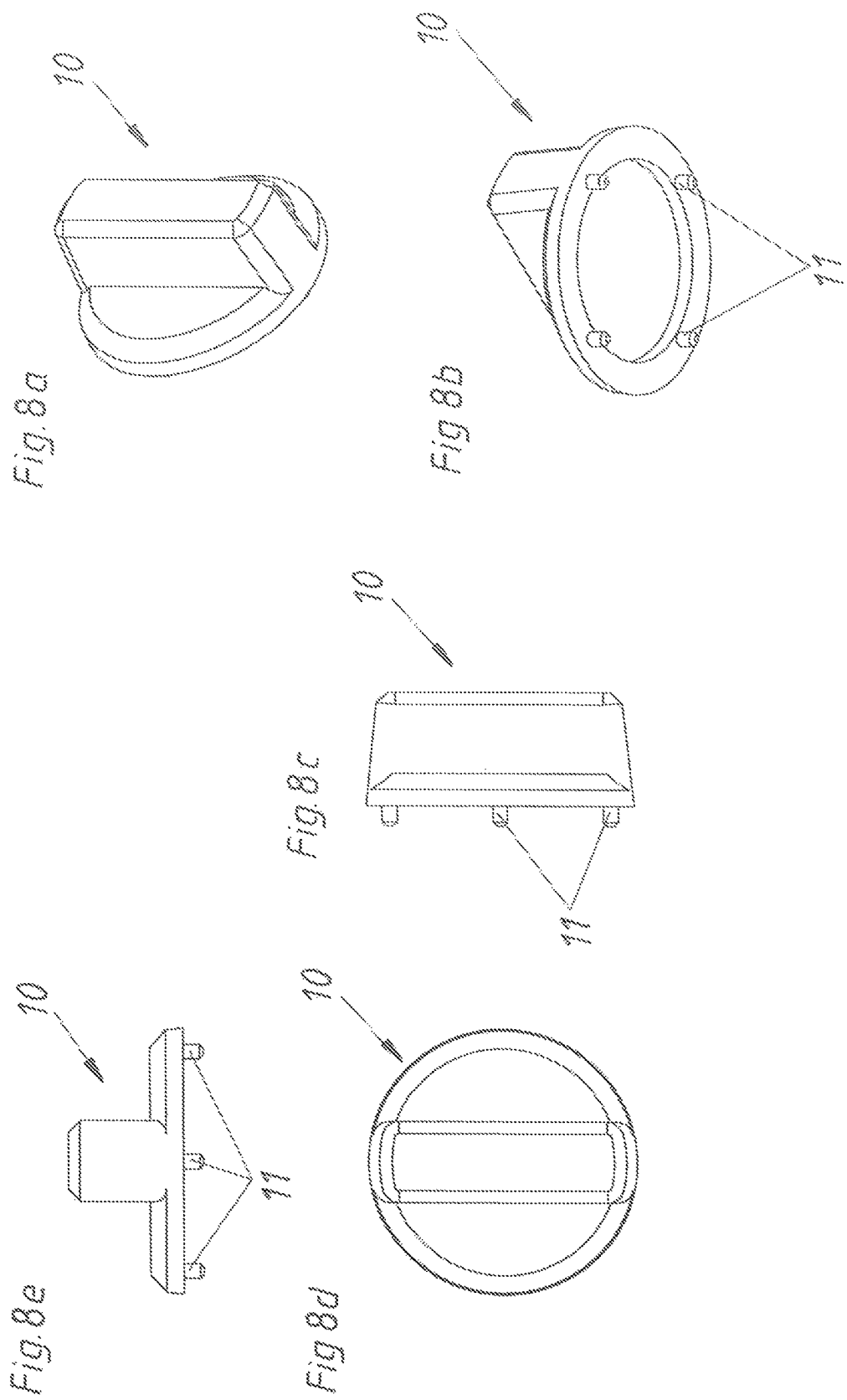

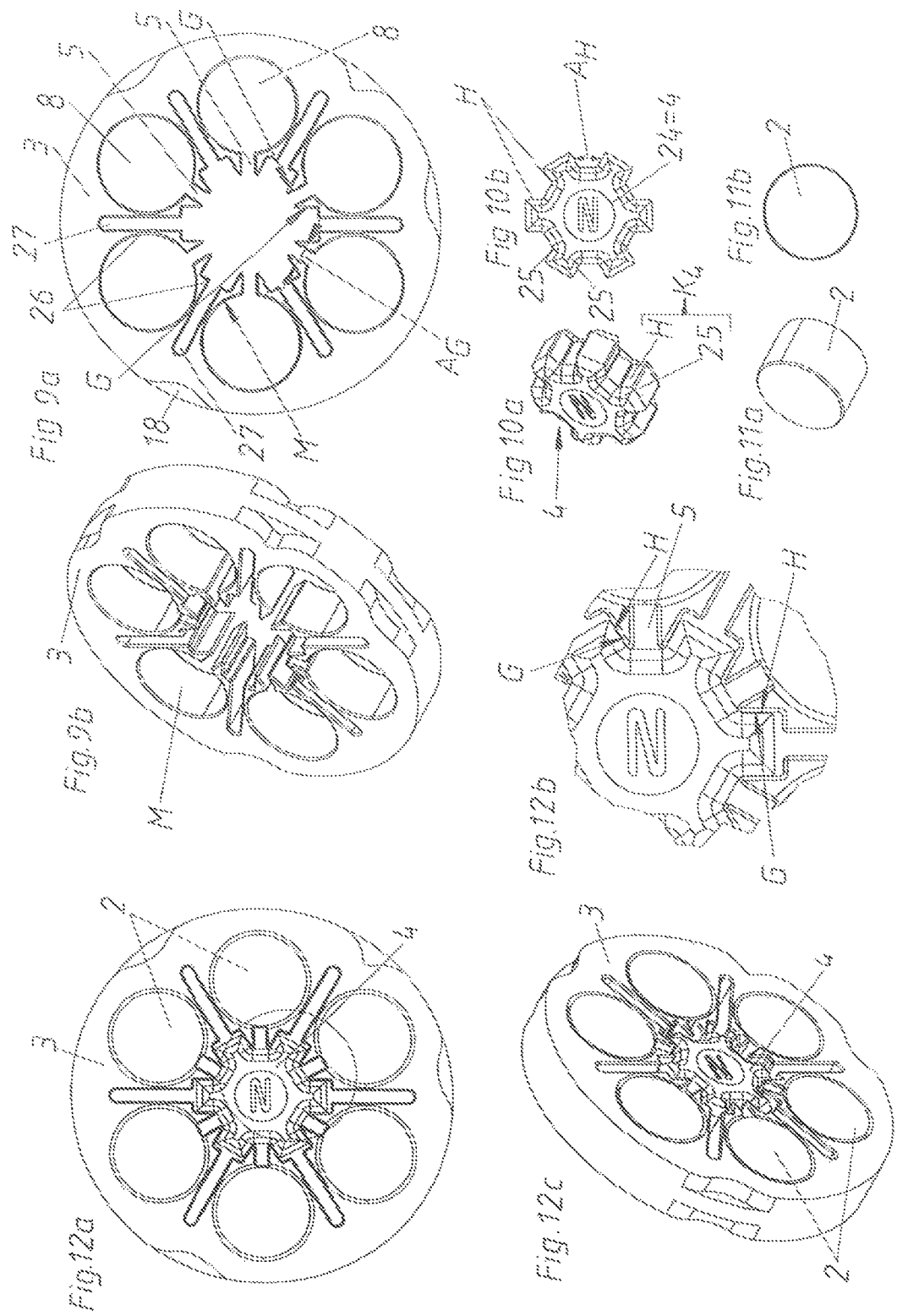

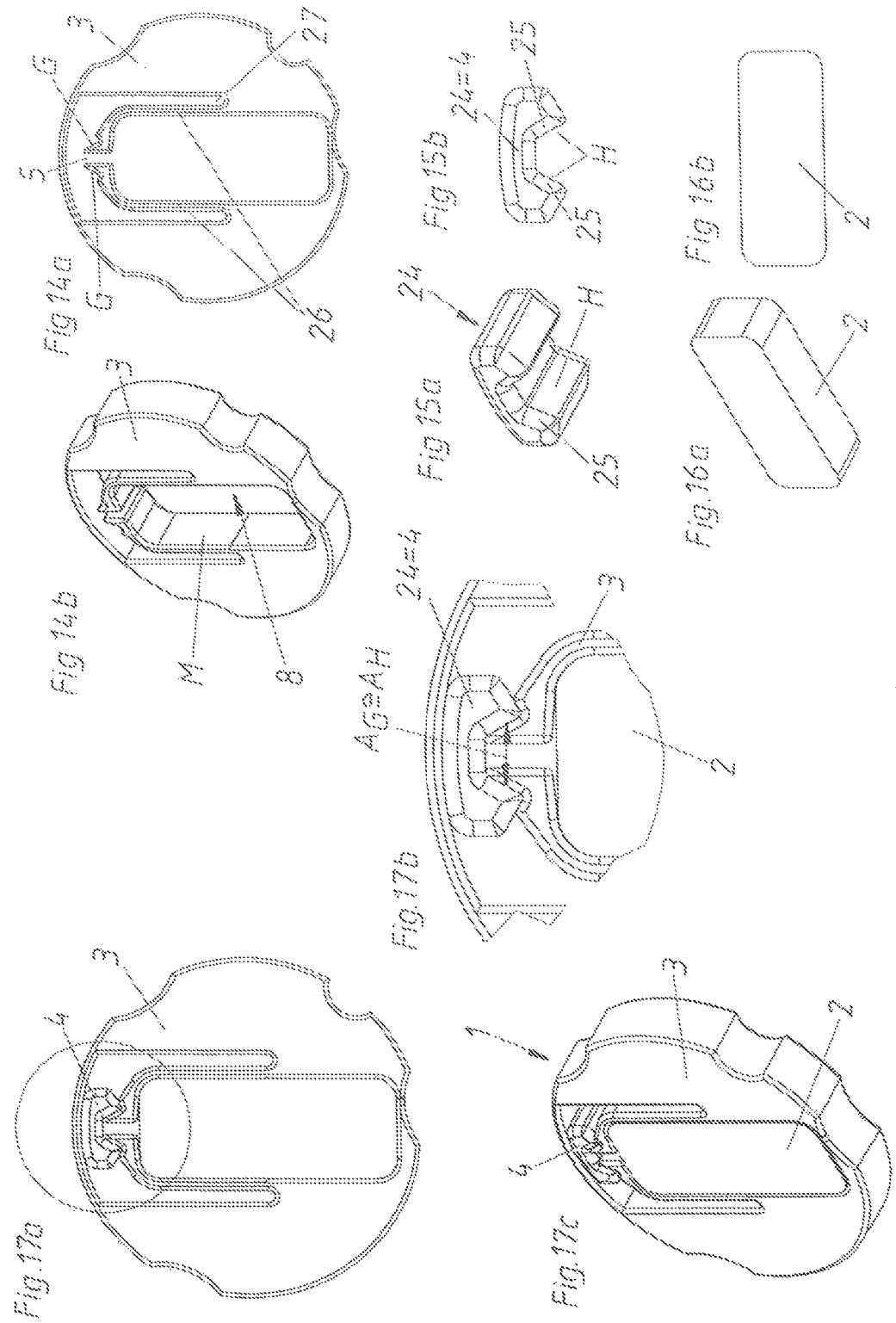

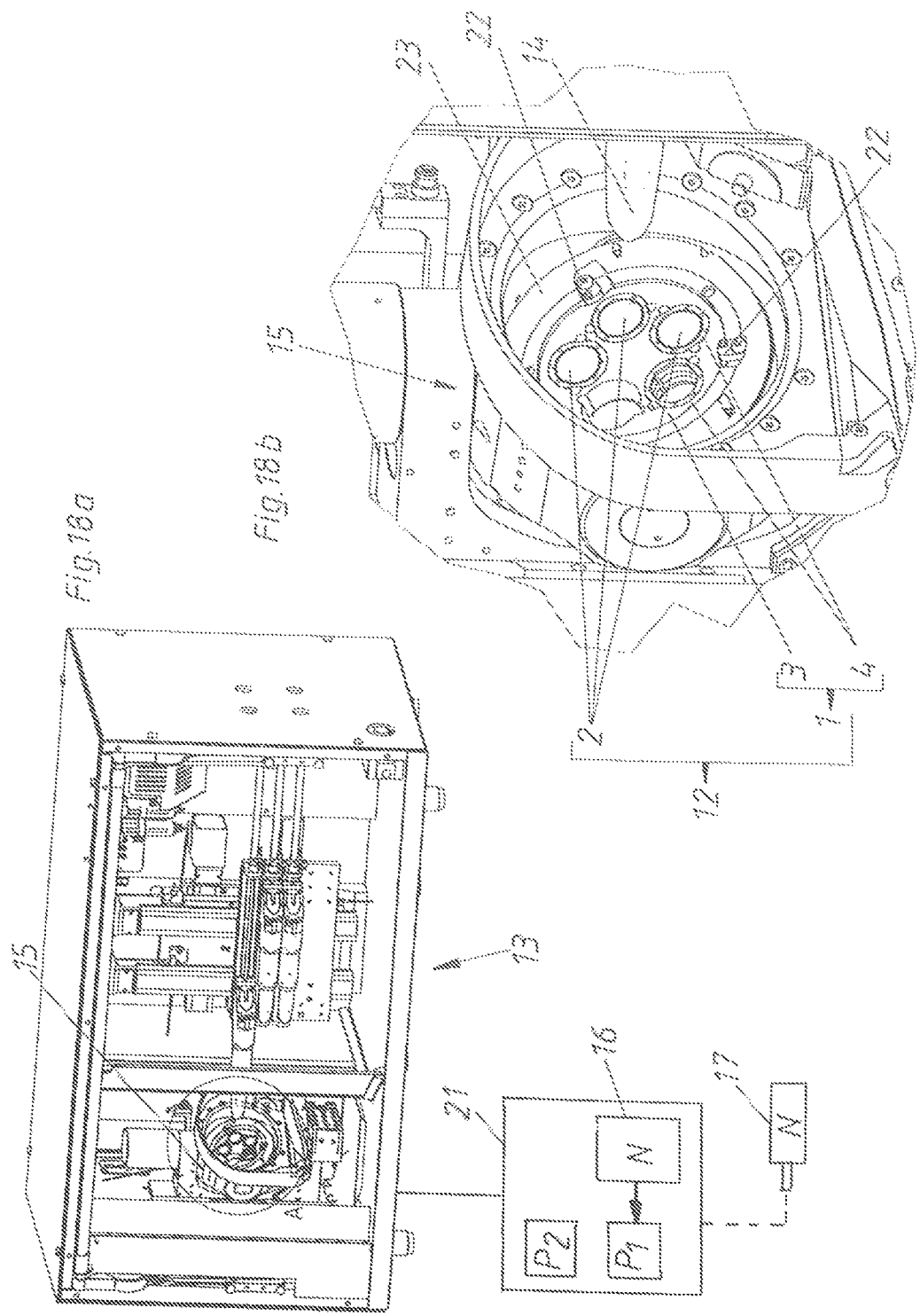

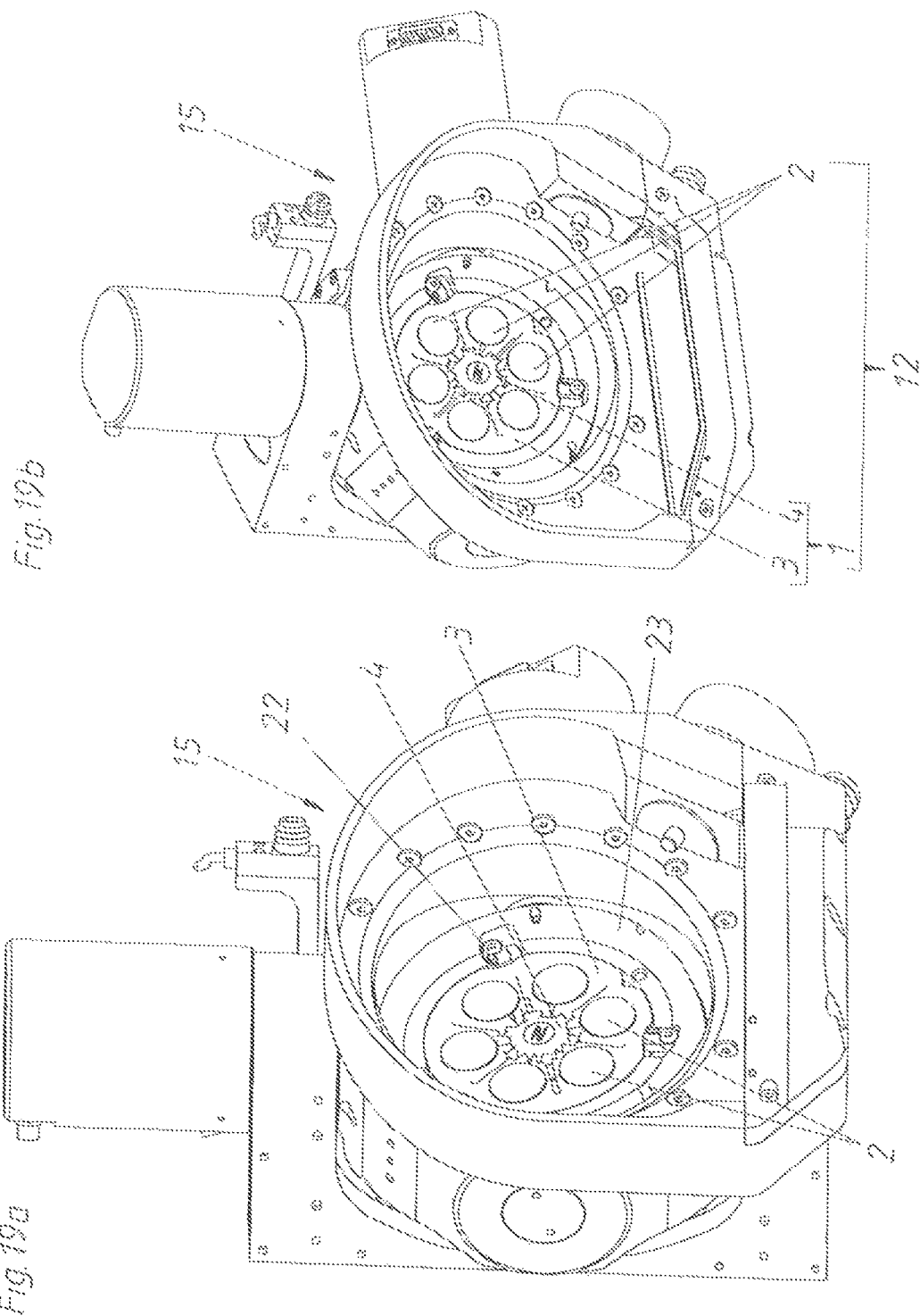

HOLDING APPARATUS FOR A DENTAL WORKPIECE

BACKGROUND OF THE INVENTION

The invention concerns a holding apparatus for, in particular, a dental workpiece comprising a holding element and a fixing device. The workpiece can be fixed to the holding apparatus by a movement of the fixing device relative to the holding element. In addition, the invention concerns a set comprising such a holding apparatus and a dental workpiece. Furthermore, the invention also concerns a processing machine having such a holding apparatus. In addition, the invention concerns a process for the production of a holding apparatus and a processing machine for carrying out that process.

Various apparatuses such as CNC machines have been used for many years in dental laboratories for producing or processing dental workpieces in an automated procedure. An important aspect in that respect is that the dental workpiece which is usually in the form of a blank is securely held so that exact processing of the dental workpiece by way of a processing tool is possible. For that purpose, there are already various holding apparatuses which usually have a kind of holding element (also referred to as a holding frame or carrier plate) and a fixing device for the workpiece on the holding element.

An example of this can be seen from DE 100 37 531 A1, which discloses an apparatus for the production of dental workpieces. In that case, an opening for a blank is provided in a carrier body. The carrier body can be gripped in a processing machine with its outside. The blank is connected only to a part of the opening. A central rectangular opening serves to receive the cylindrical blank. The blank is glued at two opposite surfaces to the corresponding walls of the opening. That adhesive mounting is relatively complicated and expensive and leaves residues behind. In addition, an embodiment having an adhesive-free holding arrangement is shown, for example, involving a mechanical positively locking connection achieved by the blank itself having two mutually opposite mushroom-shaped projections which engage into an opening. A disadvantage with this variant is that the blank itself must have a relatively complicated configuration. In addition, the loading on the blanks in the region of the projections or in the enlarged region is relatively high. With this direct connection variant, damage to the blank cannot be excluded, in particular due to the high pressure loading.

A further holding arrangement for workpieces is disclosed in EP 2 026 931 B1. In accordance therewith, a clamping frame has an opening in which inwardly freely projecting support portions are provided on the clamping frame. A clamping device is also provided on the clamping frame. A frame-shaped holding arrangement can be secured to the clamping frame by that clamping device. Once again, the workpiece is glued or welded in that holding apparatus, and is preferably held in force-locking and/or positively locking relationship. It is stated generally that the workpiece together with the holding arrangement can be fitted fixedly and non-displaceably in a cutting machining apparatus by a clamping device, more specifically on a clamping frame which can be inserted therein. However, that specification does not explain how precisely the force-locking and/or positively locking connection between the workpiece and the holding arrangement is made.

US 2009/0274994 A1 discloses a dental milling machine based on a CNC machine. In this case, the individual blanks are fixed to the holding frame by a projection. The precise fixing mode is not described in greater detail, rather this involves being able to fit smaller or larger blanks.

DE 20 2010 001 125 U1 also shows an apparatus for holding and/or gripping blanks serving for the production of dental prostheses. For that purpose, an outer annular receiving device having a receiving opening is provided. The blank can be held in the receiving device directly by clamping means or clamping claws. It is, however, also possible for an adaptor to be fitted into the receiving device instead of a large blank, in which case in turn a blank or a plurality of blanks are mounted to the adaptor. The clamping claws are mounted releasably or interchangeably to the receiving device, and it is possible to use clamping claws of varying lengths to hold blanks of differing thicknesses. A disadvantage here is that the clamping claws bear directly against a relatively small region of the blank, whereby a relatively high pressure acts on the blank in that region. That can lead to unwanted deformation or overloading of the blank material.

In addition, WO 2013/117540 A1 shows a blank receiving means for a dental milling machine. Accordingly, there is an outer gripping holder and an inner workpiece holder on which in turn a support projection for the blank is provided. The arrangement further includes a clamping device which presses the blank against the support projection. The clamping device is releasably mounted by screw bolts to the workpiece holder. This, therefore, involves a clamping action for the blank between the clamping device and the support projection. Here, too, there is the disadvantage that direct clamping is effected in a small region of the blank and the blank must be of a relatively complicated shape. In addition, relatively many components are required for the fixing action.

DE 41 37 563 C1 discloses an apparatus for receiving workpieces of varying dimensions, and blanks of a differing external contour are gripped between prism carriers. Cam projections are provided for uniform opening at both sides, the projections engaging into semicircular recesses in a curved body. Due to the curved contour of the recesses, the displacement travel that the prism carriers cover is identical and in each case of the same magnitude, relative to the theoretical central axis. That, therefore, gives a curved narrowing of clamping surfaces. In this case, too, a relatively large number of components are required for the fixing action.

DE 10 2010 061 116 A1 also discloses a process for the production of dental workpieces, in which a workpiece is connected to a glued frame for fixing in a workpiece holder by a clamping action. In that case, the workpiece itself can be provided with a projecting step or with a notch into which a congruent counterpart portion of the clamping device engages in the region of an axis in the form of a wedge. That clamping or wedge action in this case is also detrimentally implemented directly at a relatively small region of the workpiece and can thus cause damage in the workpiece to be held.

SUMMARY OF THE INVENTION

Therefore, the object of the present invention is to provide a holding apparatus which is improved over the state of the art or an alternative holding apparatus. In particular, the invention seeks to provide that the holding apparatus has a structurally simple configuration and a secure hold for the workpiece can be guaranteed.

The object is achieved by a fixing device or a holding element having a split sleeve, in which the inside surface of the split sleeve forms a clamping surface for the workpiece. Upon relative movement of the fixing device with respect to the holding element, the workpiece can be braced against the holding device by the clamping surface. That split sleeve therefore permits peripheral fixing of the workpiece to the holding apparatus. Advantageously, the securing force is distributed to a large region of the workpiece. The holding apparatus according to the invention can also be used or employed in the state of the art as an improved holding option for a workpiece.

The precise configuration of the split sleeve can be any desired kind as long as the workpiece is braced to the holding apparatus by the relative movement between the holding element and the fixing device. Preferably, however, the split sleeve has a part-annular configuration around a longitudinal axis with a preferably axially directed slit. The slit in that case serves in particular to provide that, in the bracing situation, the split sleeve is constricted and thereby the workpiece is clamped fast to the holding apparatus.

Particularly preferably, the clamping surface of the split sleeve can be applied against the workpiece, and the clamping surface has a first inside diameter corresponding to a loose condition of the split sleeve. The clamping surface can be reduced to a second inside diameter corresponding to a braced condition of the split sleeve by the relative movement of the fixing device with respect to the holding element with a narrowing of the slit. Particularly, if the split sleeve is designed on the basis of a circular cylinder, the constriction of the split sleeve can also be defined by the inside diameter instead of by the internal width.

Further preferably, the holding element and the fixing device have corresponding guide or wedge surfaces. The fixing device can be fixed, preferably by wedging, against the holding element by the relative movement of the fixing device with respect to the holding element by the guide or wedge surfaces which bear against each other. The movement along the guide or wedge surfaces provides that the clearances which are often present between holding element, fixing device and workpiece can be better compensated for. In other words, if there are small differences in the actual dimensions of the components involved, the fixing or wedging action will nonetheless always guarantee a secure stable hold in respect of the fixing device on the holding element and thus the workpiece on the holding apparatus.

In regard to the configuration and arrangement of the split sleeve, two different embodiments are discussed in detail in this application. According to a first embodiment, the split sleeve is provided separately from the holding element as part of the fixing device. According to a second embodiment—which is discussed in greater detail hereinafter—the split sleeve is in one piece with the holding element. The first embodiment will be discussed in greater detail hereinafter.

In regard to the first embodiment, the exact design configuration of the guide or wedge surfaces can be of any desired nature. For example, the guide or wedge surfaces can be in the form of planes. Preferably, however, the guide or wedge surfaces at least partially have a conical configuration. In other words, conical means that the guide or wedge surfaces are at least partially in the form of a surface of a cone. Besides the pure wedging action, that also permits a centering effect.

In addition, preferably the guide or wedge surface of the holding element is formed by an at least partially conical inside surface of the holding element. Thus, the holding element forms an outer component of the holding apparatus, and the inside surface forms the guide or wedge surface. In matching relationship therewith, the guide or wedge surface of the fixing device can be formed by an at least partially conical outside surface of the fixing device. Thus, the fixing device forms an internal component of the holding apparatus.

In principle, a purely linear movement is sufficient for making the connection between the fixing device and the holding element. In addition, a rotational component may also be involved in the relative movement. It is sufficient therefore that a dental technician positions the holding element, the fixing device, and the dental workpiece by hand, and a wedging effect is effected by pushing in or displacing the fitting device relative to the holding element whereby at the same time the dental workpiece is clamped fast to the holding apparatus. Preferably, however, the holding apparatus itself also has additional guide components so that the relative movement for the fixing action can be effected in guided relationship.

According to a preferred embodiment, at least one preferably at least partially thread-shaped guide is provided in the holding element and the fixing device has at least one nose engaging into the guide. The guide or wedge surfaces of the fixing device and the holding element move relative to each other in the axial direction and wedge by virtue of rotation of the fixing device with the nose engaging into the guide. A reversed configuration (guide in the fixing device and nose on the holding element) is also conceivable.

Further preferably, the guide or wedge surface of the holding element defines an opening in the holding element and the opening provides a wide side and a narrow side. The maximum diameter of the opening on the wide side is greater than the maximum diameter of the opening on the narrow side.

To cause the axial relative movement for fixing or wedging, preferably the guide has a guide surface which is inclined relative to a transverse plane oriented at a right angle relative to the longitudinal axis, preferably being inclined through an angle of between 2° and 15°. To also produce the desired direction for the relative movement, preferably the guide surface is inclined in the direction of the narrow side.

It is per se immaterial where precisely the guide means is provided as long as the nose can engage into the guide. Thus, the guide can certainly be provided in the central region or in the region of the wide side. According to a preferred variant, however, the guide is provided in the region of the narrow side of the opening in the holding element.

In order to be able to guarantee appropriate positioning when the fixing device is put together with the holding element, preferably in the holding element is at least one axially oriented groove which also forms the inside surface and corresponds to the at least one nose. More specifically in that case, positioning is effected by the fixing device being guided on the holding element by the nose engaging into the groove whereby the fixing device is linearly axially moveable along the groove in the relative movement.

For user-friendly and intuitive positioning and fixing, preferably the groove and the guide blend into each other whereby the groove and the guide by the cooperation with the nose of the fixing device predetermine the relative movement in the form of a bayonet closure-like fixing movement for the fixing device on the holding element.

Besides the holding element and the fixing device, the holding apparatus according to the first embodiment can also have a tool for carrying out the relative movement of the fixing device with respect to the holding element. Thus, the dental technician does not have to connect only with his hands the two components consisting of the holding element and the fixing device. Preferably, the tool has connecting elements for connection in positively locking relationship to the fixing device, and the fixing device is at least rotatable relative to the holding element by the tool.

Accordingly, matching counterpart connecting portions in relation to the connecting elements of the tool can be provided in the fixing device.

In the second embodiment—in which the split sleeve is part of the holding element—preferably the fixing device has at least one clamp with two mutually spaced clamp surfaces—which correspond to the guide or wedge surface of the fixing device. The clamp surfaces of the fixing device can be applied against mutually spaced counterpart clamp surfaces arranged in the region of the slit facing away from the clamping surface—and which correspond to the guide or wedge surface of the holding element.

To permit fixing or wedging between holding element and fixing device in a simple fashion, preferably the mutually spaced clamp surfaces have a minimum spacing relative to each other, which is less than the spacing between the counterpart clamp surfaces in the loose condition of the split sleeve.

In order to permit the connection to be made at all between holding element and fixing device, guide portions which are preferably inclinedly oriented are provided at the clamp surfaces of the fixing device. For that purpose, preferably the counterpart clamp surfaces are moveable relative to each other by the relative movement of the clamp with respect to the holding element by the guide portion which bears against the counterpart clamp surfaces so that with a reduction in the slit the clamping surface can be reduced to the second inside diameter which corresponds to the braced condition of the split sleeve and in which the minimum spacing of the clamp surfaces relative to each other is equal to the spacing between the counterpart clamp surfaces.

Further preferably, a plurality of separate workpieces can be braced to the holding apparatus by respective split sleeves. In this case, there can be an associated clamp for each split sleeve. In other words, the fixing device has at least two clamps which are preferably arranged regularly relative to each other, and each clamp respectively corresponds to one of at least two split sleeves provided in the holding element.

In order also to be able to clamp a plurality of workpieces fast as quickly as possible, it is particularly preferable that the fixing device having a plurality of clamps is in one piece. Thus, a plurality of workpieces can be simultaneously braced to the holding apparatus by the relative movement of that single one-piece fixing device. Preferably, the fixing device has a star-shaped configuration for that purpose.

It is certainly also possible that at least one workpiece, preferably a plurality of prefabricated workpieces, is also included. A set can also include a holding apparatus according to the invention and at least one dental workpiece. In that respect, that workpiece can have widely varying shapes. For ease of production and mounting, the workpiece is in the form of a right circular cylinder.

A processing machine, in particular a CNC machine, includes a processing tool and a holding apparatus as described above for processing and holding a workpiece. To permit movement of the gripped or clamped workpiece, preferably the processing machine has a moveable positioning device which preferably has a cardan joint-like configuration, and the holding apparatus can be releasably fixed on the positioning device. The workpiece can then be processed in a dental workpiece production mode by the processing tool using that machine.

Furthermore, a process for the production of a holding apparatus according to the invention involves a processing machine, in particular in a CNC machine. That process can be implemented in the same processing machine in which processing of the workpiece is also effected. Here, it is particularly preferable that in a holding apparatus production mode of the processing machine, the holding element and the fixing device of the holding apparatus can be produced, preferably milled, from workpieces clamped in the processing machine. That is preferably effected by the holding apparatus production mode being performed on the basis of data of the holding element and the fixing device, which are stored in a memory and which can be read and executed by the processing machine.

Protection, however, is not only requested for the processing machine with a holding apparatus according to the invention, but also for a processing machine for carrying out the process for the production of a holding apparatus. In that respect, the holding apparatus production mode for production of the holding apparatus is stored in a memory of the processing machine, and the holding apparatus production mode can be enabled by input of a code. Thus, in regard to future deliveries of processing machines, the corresponding holding apparatus production mode can already be stored in the processing machine. If the owner or purchaser of that processing machine then also desires his own production of the holding apparatus according to the invention, he can cause the corresponding holding apparatus production mode to be enabled.

Alternatively, however, it is also conceivable for a purchaser to retro-fit his already existing processing machine with a holding apparatus production mode. For that reason, protection is also claimed for a data carrier on which the production process according to the invention is stored in the form of data which can be read by a processing machine and which can be executed as the holding apparatus production mode for production of the holding apparatus.

BRIEF DESCRIPTION OF THE DRAWINGS

Further details and advantages of the present invention will be described more fully hereinafter by means of the specific description with reference to the embodiments by way of example illustrated in the drawings, in which:

FIGS. 3a and 3b are different views of a fixing device, FIGS. 4a through 4c are different views of a holding apparatus when viewing from the narrow side, FIGS. 5a through 5d are different views of the holding apparatus when viewing from the wide side, FIGS. 6a through 6d show the holding apparatus in the loose condition of the split sleeve, FIGS. 8a through 8e are various views of a tool, FIGS. 9a and 9b are views of a second embodiment of a holding apparatus, FIGS. 10a and 10b are views of the fixing device, FIGS. 11a and 11b are views of the workpiece, FIGS. 12a through 12c are views of the holding apparatus with the braced split sleeve, FIGS. 13a and 13b diagrammatically show the difference between the loose and the braced split sleeve, FIGS. 14a through 17c are views of a further variant of the second embodiment, FIG. 18a shows a processing machine with a diagrammatically illustrated open-loop or closed-loop control unit, FIG. 18b shows the detail of the positioning device of FIG. 18a, and FIGS. 19a and 19b show the processing machine with a holding apparatus according to the second embodiment.

DETAILED DESCRIPTION OF THE INVENTION

Figure 1C:
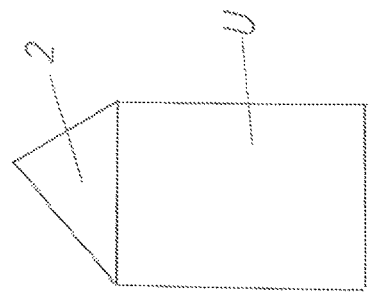
FIGS. 1a through is show variants of a dental workpiece.
Figure 1B:
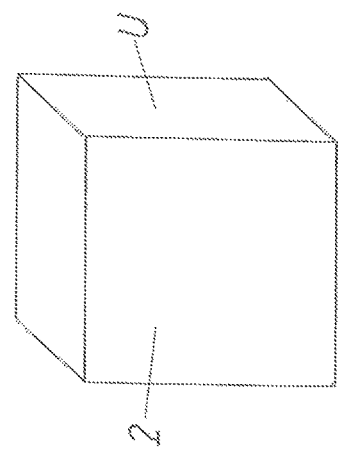
Figure 1A:
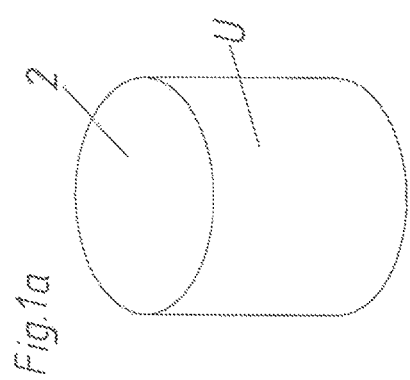

The fundamental idea of the present invention is based on the fixing of geometrically simple dental workpieces. Those dental workpieces 2 are preferably made from zirconium dioxide. It is, however, also possible to use other materials such as plastics, sintered metals, mixed materials and so forth. A preferred variant of such a zirconium block or dental workpiece 2 is shown in FIG. 1a, in accordance with which the dental workpiece 2 has a circular-cylindrical configuration and has no further steps or recesses, by way of which the dental workpiece 2 is supported or which would permit fixing. Fixing to a holding apparatus 1 is thereby effected purely in force-locking relationship. That force-locking connection is made by the peripheral surface U of the dental workpiece 2. FIGS. 1b and 1c also show alternative possible configurations of the dental workpiece 2 on the basis of a rectangular base surface or a triangular base surface.

Figure 2:
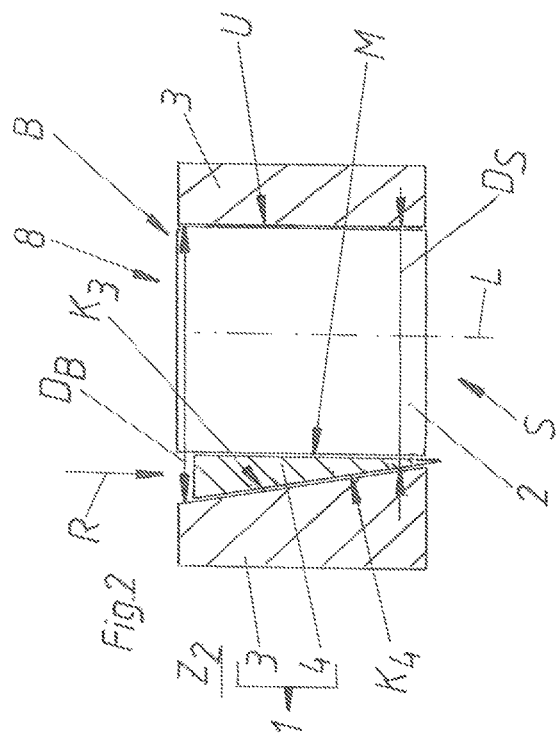
FIG. 2 shows a diagrammatic section through a first embodiment of a holding apparatus.
Figure 7D:
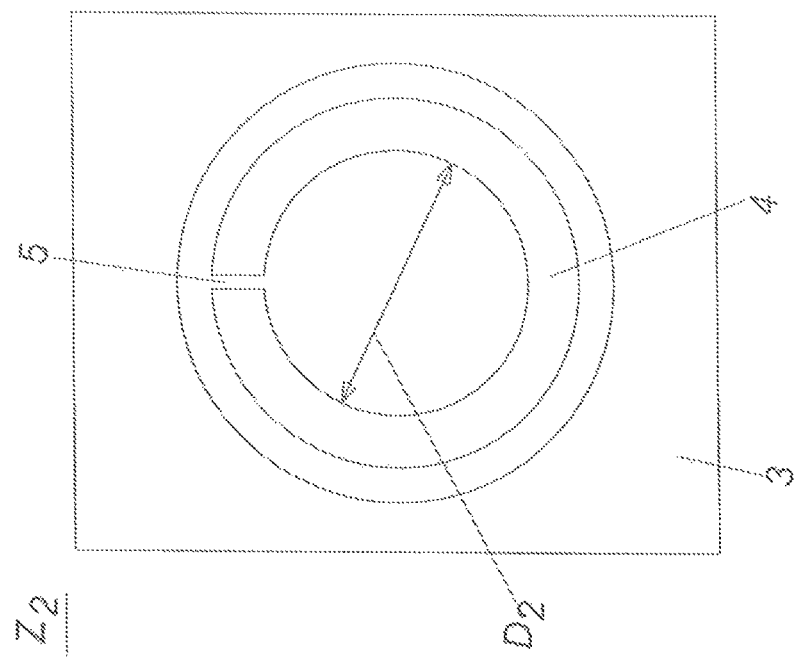
FIGS. 7a through 7d show the holding apparatus in the braced condition of the split sleeve.

FIG. 2 diagrammatically shows the fixing of a dental workpiece 2 to a holding apparatus 1. For that purpose, the holding apparatus 1 has two components, namely the holding element 3 and the fixing device 4. In the fixing operation, the workpiece 2 is first introduced into the opening 8 in the holding element 3. At the same time, the fixing device 4 is also pre-positioned. In that case, as shown in FIG. 2, the fixing device 4 is in the form (in section) of a simple wedge. In that case, the fixing device 4 has a guide or wedge surface $K_4$ corresponding to the guide or wedge surface $K_3$ forming the inside surface of the holding element 3. That guide or wedge surface $K_3$ of the holding element 3 provides that the maximum diameter $D_B$ of the opening 8 on the wide side B of the holding element 3 is larger than the maximum diameter $D_S$ of the opening 8 on the narrow side S. Accordingly, the opening 8 narrows from the wide side B towards the narrow side S (this corresponds to the first embodiment). By virtue of a relative movement R of the fixing device 4 in the direction of the longitudinal axis L, the guide or wedge surfaces $K_3$ and $K_4$ move against each other whereby the peripheral surface U of the dental workpiece 2 is braced or clamped between the clamping surface M, remote from the guide or wedge surface $K_4$, of the split sleeve of the fixing device 4 and the holding element 3. In that case as shown in FIG. 2, direct contact occurs on the right-hand side between the workpiece 2 and the holding element 3. Naturally, however, it is also possible—as also shown in later embodiments—that the fixing device 4 has a configuration or is arranged in the form of a partial ring (and thus also at the right-hand side) around the dental workpiece 2. The simplest functional variant of the holding apparatus 1 is however shown in FIG. 2. Due to the relative movement R of the fixing device 4 in the direction of the arrow, the workpiece 2 therefore goes from a loose condition $Z_1$ into a braced condition in which the split sleeve is in a fixed or wedged condition $Z_2$ on the holding apparatus 1. In that braced condition $Z_2$, the space for the dental workpiece 2 within the holding apparatus 1 is constricted in such a way that the dental workpiece 2 is braced to the holding apparatus 1 and is thus clamped or gripped in force-locking relationship.

FIGS. 3 through 8e show a first embodiment of a holding apparatus 1. In comparison with the structure shown in FIG. 2, it can be seen from FIG. 3a that the fixing device 4 is in the form of a partial ring and thus forms the split sleeve. For that purpose, the split sleeve of the fixing device 4 has a slit 5. The slit 5 does not have to be continuous therethrough, and instead may also be only of such a length as to permit a reduction in the inside diameter D. The slit 5 also does not have to be in the form of an opening or "free space" but can also be filled with a yielding material. In addition, the slit 5 does not have to be oriented precisely in the axial direction but can certainly also be oriented inclinedly and thus not parallel to the longitudinal axis L. Preferably, however, the slit 5 extends continuously through the sleeve and is oriented in the axial direction. At the outside or at the outside surface the fixing device 4 is the guide or wedge surface $K_4$. The clamping surface M is provided at the inside surface of the fixing device 4. The clamping surface can in principle have a continuously flat or level configuration so that in the braced condition $Z_2$ it bears throughout flat or flush against the workpiece 2. The specific embodiment of FIG. 3a, however, has recesses 20. Those recesses 20 or turned grooves provide for a better hold for the dental workpiece 2. Those recesses 20 can also have a spiral configuration or can have other shapes which serve for the purpose of better fixing.

FIG. 3b shows a side view of the fixing device 4. The conical configuration of the guide or wedge surface $K_4$ can be particularly well seen here. Preferably, the guide or wedge surface $K_4$ (like also the guide or wedge surface $K_3$) is inclined relative to the longitudinal axis L through an angle β of between 1° and 15°, preferably between 2° and 10°.

FIG. 4a shows the holding apparatus 1 with a view on to the narrow side S of the holding element 3. Provided in the holding element 3 are a total of five openings 8 which respectively form an inside, guide or wedge surface $K_3$ of the holding element 3. In addition, the guide surfaces F of the guide 6 can be seen in FIG. 4a. They correspond to the noses 7 on the fixing device 4. The grooves 9 in the holding element 3, oriented in the axial direction, can also be seen.

It is also possible to see the slit 5 in each fixing device 4. Arranged regularly at the rim surface of the holding element 3 are the clamping surfaces 18, by way of which the entire holding apparatus 1 is releasably fixed to a positioning device 15 of a processing machine 13.

FIG. 4b shows the section i-i through the holding apparatus 1 of FIG. 4a. It can be seen that the guide 6 is provided at the narrow side S of the holding element 3. In this arrangement, the guide 6 merges into the groove 9. It is also possible to see the guide surface F of the guide 6, which is inclined in the direction of the narrow side S through the angle α relative to the transverse plane Q oriented at a right angle to the longitudinal axis L. That configuration provides that, when the nose 7 of the fixing device 4 bears against the guide surface F upon rotation of the fixing device 4 relative to the holding element 3, a necessary relative movement R of the fixing device 4 in the direction of the longitudinal axis L towards the narrow side S takes place, whereby the wedge or guide surfaces $K_3$ and $K_4$ wedge together.

FIG. 4c shows a perspective view of the holding apparatus 1 again viewed in the direction of the narrow side S. It can be seen that the fixing devices 4 are still in the loose condition $Z_1$. A slight wedging effect between the guide or wedge surfaces $K_3$ and $K_4$ may, however, already exist. That, however, is still not sufficient to adequately clamp a dental workpiece 2 (not shown in this FIG. 4c) within the fixing device 4.

FIGS. 5a through 5d show the same embodiment and the same condition $Z_1$ as FIGS. 4a through 4c. FIG. 5a, however, shows the holding element 3 together with the fixing device 4 from the wide side B. The counterpart connecting portions 19 which are provided in the fixing device 4 for receiving the tool 10 which is also shown hereinafter can also be seen from the wide side B.

FIG. 5b shows a side view of the holding element 3, clearly illustrating the clamping surfaces 18.

FIG. 5c shows the section ii-ii through the holding apparatus 1 of FIG. 5a. It is possible to see the mutually contacting conical guide or wedge surfaces $K_3$ and $K_4$ of the holding element 3 and the fixing device 4 respectively.

FIG. 5d shows a perspective view of the holding apparatus 1 viewed in the direction of the wide side B. The transition from the axially oriented groove 9 into the guide 6 which is oriented slightly inclinedly relative to the transverse plane Q can be clearly seen. The relative movement R of the fixing device 4 with respect to the holding element 3 is shown in broken lines in this FIG. 5d. The positive guidance is effected by the nose 7 of the fixing device 4, that corresponds to the groove 9 and the guide 6. That relative movement R forms a bayonet closure-like fixing movement for the fixing device 4 on the holding element 3.

FIG. 6a shows the holding apparatus 1 in a loose condition $Z_1$ of the fixing device 4. Nonetheless, a dental workpiece 2 is already disposed in the holding apparatus 1.

It can be seen from FIG. 6b that the slit 5 in the split sleeve of the fixing device 4 is still opened. As a result, there is still no adequate clamping between the dental workpiece 2 and the holding apparatus 1. FIG. 6b also shows that the holding apparatus 1 is formed by the fixing device 4 and the holding element 3. The holding apparatus 1 in turn forms the set 12, together with the at least one dental workpiece 2.

FIG. 6c shows the section iii-iii through the set 12 of FIG. 6b. The clamping surface M, which can bear against the workpiece 2, of the split sleeve of the fixing device 4 still has a first inside diameter $D_1$ corresponding to a loose condition $Z_1$ of the fixing device 4.

Figure 6D:
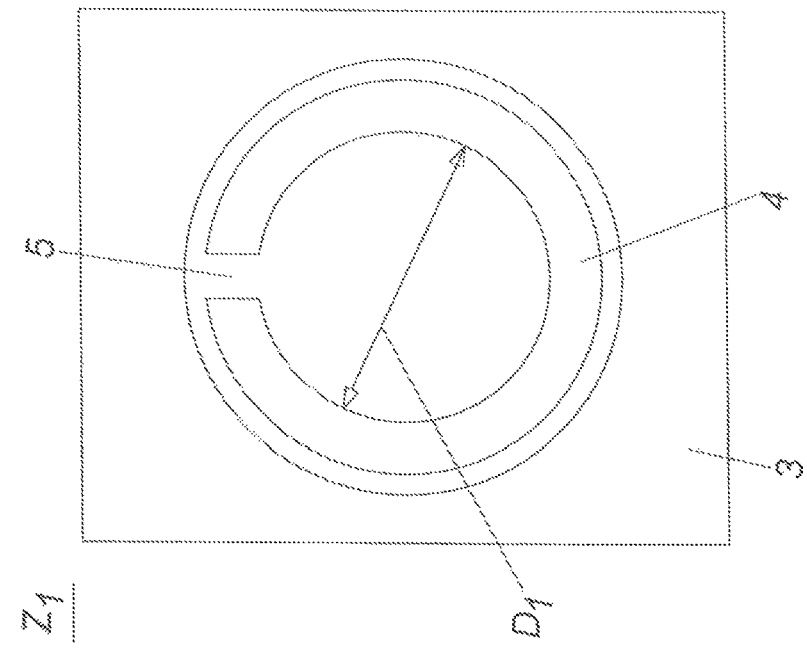
Figure 7A:
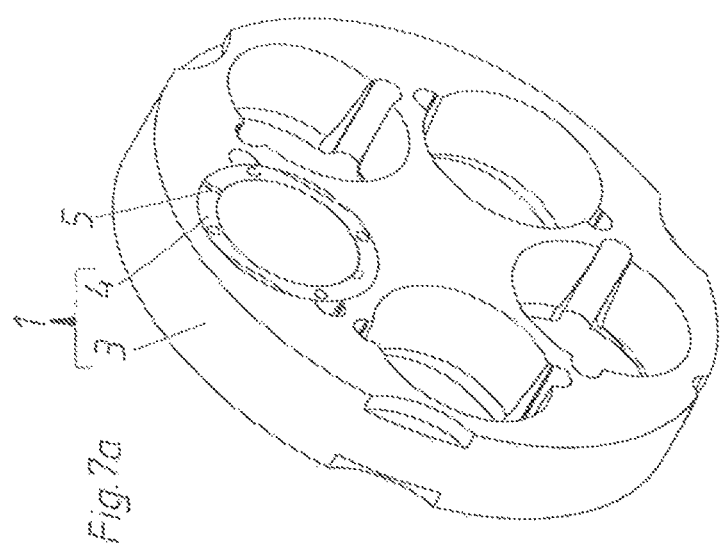
Figure 7B:
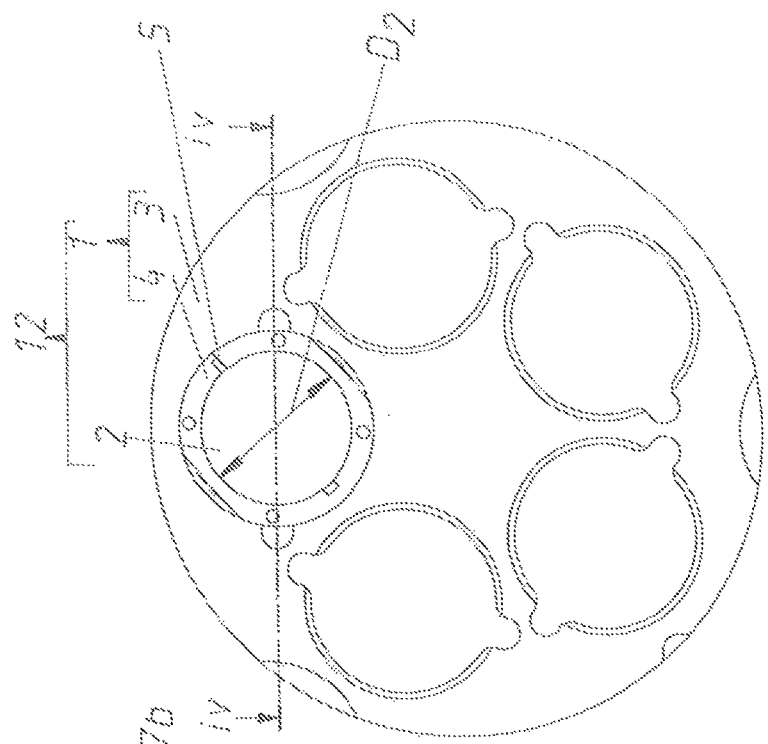
Figure 7C:
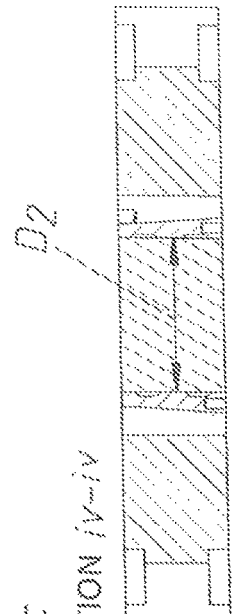

FIG. 6d also shows that larger inside diameter $D_1$ when the slit 5 is still open.

In comparison, FIGS. 7a through 7d show the holding apparatus 1 in the wedged condition $Z_2$ of the fixing device 4 on the holding element 3. As can be seen in that respect from FIG. 7a, the slit 5 of the split sleeve of the fixing device 4 has already constricted whereby the clamping surface M bears flush against the peripheral surface U of the workpiece 2. That constriction of the slit 5 can also be seen from FIG. 7b, whereby the clamping surface M of the fixing device 4 is reduced to a second inside diameter $D_2$ corresponding to a braced condition $Z_2$ of the split sleeve of the fixing device 4. That reduced second inside diameter $D_2$ can also be seen from FIGS. 7c and 7d. In particular, a comparison of FIGS. 6d and 7d—shown diagrammatically and in exaggerated form—shows the change in diameter between the loose condition $Z_1$ and the braced condition $Z_2$.

FIGS. 8a through 8e show various views of the tool 10 having the connecting elements 11 in the form of projections. Those connecting elements 11 correspond to the counterpart connecting portions 19 provided in the fixing device 4. When such a tool 10 is fitted to a fixing device 4 as shown in FIG. 6a, then the nose 7 is also moved along the guide surface F of the guide 6 by rotation on the tool 10 so that the fixing device 4 moves relative to the holding element 3 in the direction of the narrow side S. As a result, the clamping surface M of the fixing device 4 is constricted, resulting in clamping of the dental workpiece 2.

FIGS. 9a through 17c show a second embodiment of a holding apparatus 1. In this second embodiment, the split sleeve is in one piece with the holding element 3.

FIG. 9a as a plan view on to the holding element 3 shows that the split sleeve substantially comprises the two bow portions (curved portions) 26 and the slit 5. In this case, the holding element has in total six such split sleeves each having two bow portions 26. As illustrated in at least FIG. 9b, the slit 5 extends along the longitudinal axis of said split sleeve (i.e., extends along the axial length of the fixing device 4 and/or the holding element 3). The inside surface of each split sleeve forms a clamping surface M for the workpiece 2. A certain flexibility of the bow portions 26 is guaranteed by the opening 27. A counterpart clamp surface G is provided on each bow portion 26 in a region remote from the clamping surface M. In the loose condition $Z_1$ of the split sleeve as shown in FIG. 9a, the counterpart clamp surfaces G of two bow portions 26 of a split sleeve are spaced from each other by the spacing $A_G$. FIG. 9b shows a perspective view of the same holding element 3.

FIGS. 10a and 10b show the fixing device 4 having a plurality of clamps 24 each having two clamp surfaces H. The total of six clamps 24 are in one piece and together form the fixing device 4. The clamp surfaces H of the clamps 24 are at a minimum spacing $A_H$ relative to each other. The clamp surfaces H together with the guide portions 25 form the guide or wedge surfaces $K_4$ of the fixing device 4. Those guide portions 25 are in the form of rounded-off or inclined edge regions of the fixing device 4.

FIGS. 11a and 11b show a workpiece 2 which can be braced to the holding apparatus 1.

Figure 13A:
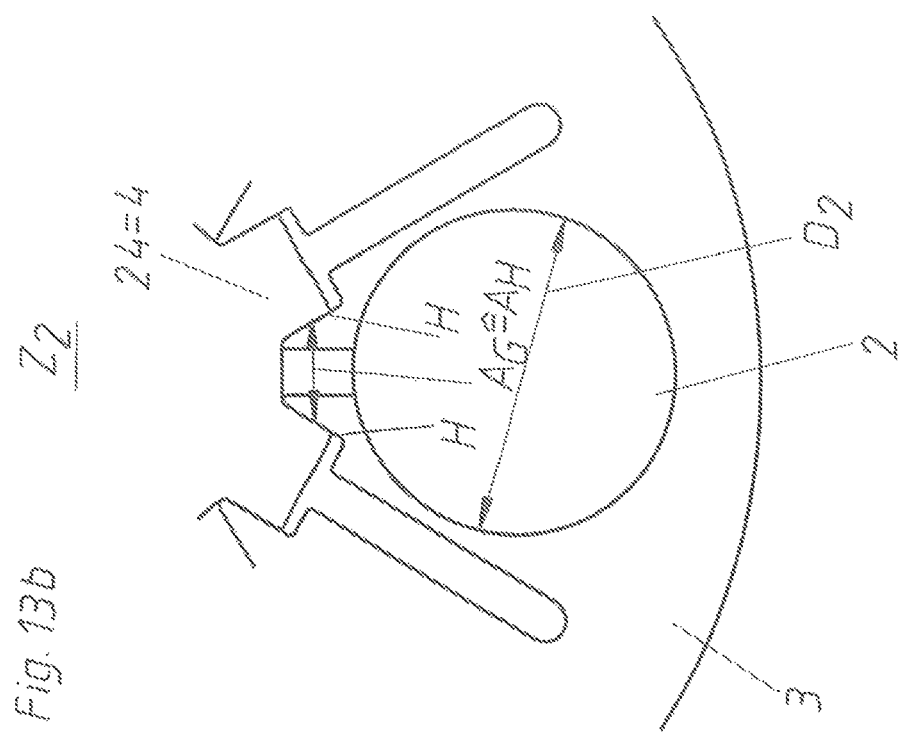

Bracing of a workpiece 2 to the holding apparatus 1 in accordance with the second embodiment is effected by the desired number of workpieces 2 firstly being fitted into a holding element 3 as shown in FIG. 9a, into the openings 8 provided for same. As the split sleeves of that holding element 3 are still in the loose condition $Z_1$, introduction of the workpieces 2 into the openings 8 is possible without any problem. The insertion of the workpiece is shown in FIG. 13a, in which the spacing $A_G$ between the counterpart clamp surfaces G and thus the size of the slit 5 are shown in exaggerated form. It can also be seen that the workpiece 2 does not (or scarcely) contact the holding element 3 as the inside diameter $D_1$ in the loose condition $Z_1$ is still larger.

Figure 13B:
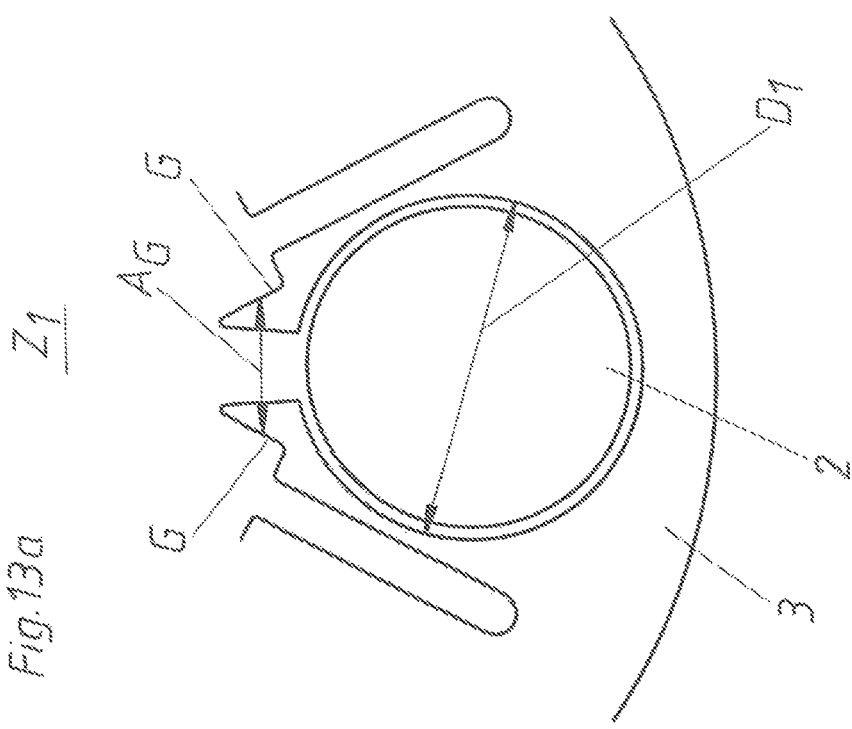

As soon as the desired number of workpieces 2 is inserted in the holding element 3, the preferably star-shaped fixing device 4 is introduced into the center of the holding element 3. In that case, the guide portions 25 initially contact the counterpart clamp surfaces G of the split sleeves of the holding element 3. By virtue of the relative movement R of the fixing device 4 in the direction of the longitudinal axis L, the bow portions 26 of the split sleeves are moved towards each other by virtue of the inclined guide portions 25 until the counterpart clamp surfaces G contact the clamp surfaces H. As a result, the spacing $A_G$ between the counterpart clamp surfaces G of a split sleeve corresponds to the minimum spacing $A_H$ between the clamp surfaces H, as shown in FIG. 13b. As the bow portions 26 move towards each other due to that relative movement R, the inside diameter $D_2$ of the split sleeve is reduced whereby the workpiece 2 is braced by the peripheral surface U against the clamping surface M of the split sleeve. FIGS. 12a through 12c show the condition when a total of six workpieces 2 are braced in a holding element 3 by a fixing device 4. It is particularly advantageous with this structure that all workpieces 2 can be simultaneously braced to the holding apparatus 1 by a single relative movement R of the fixing device 4 relative to the holding element 3. It is also possible for some openings 8 to be left free and also, for example, only a single workpiece 2 to be fixed in such a holding element 3.

FIGS. 14*a* through 17*c* show a further variant of the second embodiment, in which only one workpiece 2 can be braced in this holding element 3. In the same fashion as with the first variant, this arrangement has a split sleeve with two bow portions 26 together with counterpart clamp surfaces G (see FIGS. 14*a* and 14*b*). The fixing device 4 in FIGS. 15*a* and 15*b* is formed by a clamp 24 having two mutually spaced clamp surfaces H. The workpiece 2 has a rectangular base surface with rounded-off side edges. As soon as that workpiece 2 is fitted into the opening 8 in the holding element 3, the fixing device 4 (clamp 24) is inserted as shown in FIGS. 17*a* through 17*c* by the guide portions 25 until the clamp surfaces H and the counterpart clamp surfaces G are in contact so that the clamping surface M holds the workpiece 2 to the holding apparatus 1. In that case, the entire inside diameter of the clamping surface M is not reduced, but the clamping surface M is pressed more intimately against the workpiece 2 by the extent of the reduction in the size of the slit 5 whereby the workpiece is sufficiently firmly braced to the holding apparatus 1.

FIG. 18*a* shows a processing machine 13 in the form of a CNC machine. In accordance with the detail view in FIG. 18*b*, that CNC machine has a positioning device 15. The positioning device 15 can have a plurality of components arranged in a cardan joint-like fashion. More specifically, provided as the innermost structural unit is a holding ring 23 to which a holding apparatus 1 or a set 12 can be releasably fixed by f the fixing element 22. The dental workpieces 2 which are held to the positioning device 15 by the holding apparatus 1 and which are moveable by that positioning device 15 can then be worked or milled by the processing tool 14. In that case, the processing operation is controlled or regulated by the open-loop or closed-loop control unit 21 diagrammatically shown in FIG. 18*a*. For that purpose, the dental workpiece production mode $M_2$ can be executed by the open-loop or closed-loop control unit 21. In addition, however, it is also possible for a holding apparatus production mode $P_1$ to be implemented by the open-loop or closed-loop control unit 21. For that purpose, data N (preferably in the form of CNC files) are stored in a memory 16 of the control unit 21. In order now to produce the holding apparatus 1 itself in the processing machine 15, the holding apparatus production mode $P_1$ can be enabled by the input of a code. As an alternative variant, it is also possible that the production mode $P_1$ can be retro-fitted to an already existing processing machine 13 by a data carrier 17 (for example a USB stick) on which the executable data N (CNC files) are stored. FIGS. 19*a* and 19*b* show the positioning device 15 with the clamped holding apparatus 1 in accordance with the second embodiment.

The invention can also be summarized and described once again using the following different words:

The fixing device 4 can also be referred as a conical counterpart portion in relation to the holding element 3 or as a clamping ring. That clamping ring can best be seen in FIG. 3*a*. Disposed on the outside of that fixing device 4 is the conical surface as the guide or wedge surface $K_4$ corresponding to a milled-out orifice or opening 8 in the holding element 3 which is in the form of a carrier plate. In the center, the fixing device 4 has a bore or opening which does not necessarily have to be concentrically positioned. Preferably, recesses 20 or turned-in grooves are provided at the inside surface of the fixing device 4, the recesses or grooves being intended to later provide for a better hold for the dental workpiece. The fixing device 4 preferably has two noses which permit assembly of the fixing device 4 and the holding element 3 only in given positions, more specifically when the noses 7 and grooves 9 are disposed precisely one above the other. When the two parts are assembled until the conical surfaces or wedge surfaces $K_3$ and $K_4$ are in contact, a further feature of the fixing device 4 comes into play. More specifically, on one side the fixing device 4 has an opening in the form of a slit 5 which preferably extends from the upper edge to the lower edge. Thus, the clamping ring (fixing device 4) is peripherally opened. When the fixing device 4 in the inserted position is turned by a wrench (tool 10) which is shown in FIGS. 8*a* through 8*d* by the auxiliary bores (counterpart connecting portions 19), that entails a reduction in the periphery of the clamping ring (inside diameter D of the clamping surface M of the fixing device 4 is reduced in size). That occurs for the reason that the noses 7 of the fixing device 4 slide over the spiral-shaped surface (guide surface F) of the holding element 3 and thus pull it in the direction of the conical narrowing. In the direction of rotation, therefore, the spacing between the front side of the holding element 3 and the surface of the guide 6 increases. To permit uniform tightening, at least two noses 7 are preferably arranged in precisely opposite relationship. However, it is also possible that more noses 7, in matching relationship also with the grooves 9 and the guides 6, are provided. They also do not have to be uniformly distributed over the periphery. The same applies to the slit 5. Accordingly, FIG. 3 only shows a preferred variant. Thus, it may be readily possible that the slit 5 does not peripherally open the fixing device 4 at one side in the longitudinal direction L, but for that purpose the arrangement has a plurality of slits 5. It will be appreciated that for such a variant, the holding element 3 must also again have the necessary structural features for satisfactory interplay.

A further substantial part of a set 12 is the block (dental workpiece 2) which preferably comprises zirconium (see in particular FIG. 1*a*). The preferred variant is a cylindrical block without any additional material removals, such as grooves extending along the periphery or region-wise protrusions. That block is then pushed into the bore of the clamping ring (fixing device 4). That can happen at the moment in time when the clamping ring is not yet disposed in the carrier plate (holding element 3) or when the clamping ring is positioned in the carrier plate but is not yet tightened, for which reason there has not yet been a reduction in periphery. Referring to FIG. 6*a*, it can be seen how the workpiece 2 is pushed into the fixing device 4 and how there is still space along the periphery between the fixing device 4 and the workpiece 2. When the fixing device 4 is rotated in the inserted position, the inside diameter D of the fixing device 4 is reduced and bears around the (in this case) periphery of the dental workpiece 2. That can be clearly seen from FIG. 7*c*. It can also be clearly seen that the pressure force produced by the cone is transmitted to the dental workpiece 2 only over certain parts of the surface of the fixing device 4. These are those regions which do not have any turned recess or the like. As rotation of the fixing device 4 always produces a similar pressure force which is then transmitted to the dental workpiece 2, the efficiency of the holding apparatus 1 can be determined by the configuration of the turned recesses therein. If the turned recesses or grooves 20 are dispensed with, the pressure force is distributed uniformly over the entire contact region. Thus, the force acting thereon, if only a small part of the surface of the dental workpiece 2 is considered, is relatively low. If now, however, the arrangement has turned grooves or recesses 20 which reduce the contact surface to half, then the same pressure force as in the above-mentioned case is now distributed to half the surface area. If once again a part of the dental workpiece 2, of the same size as previously, is considered, being acted upon with the pressure force, then that gives a holding force which is twice as great. With a certain force there is, however, inevitably deformation of the dental workpiece 2. That may happen intentionally but also unintentionally. A slight degree of deformation promotes stability in the axial direction. However, the block which is reduced in volume after a processing operation is regionwise weakened and thus more unstable. The variants shown in FIGS. 3 through 13a always relate to a circular-cylindrical block. With the dimensioning and the structural configuration being right, however, that principle can also be transferred to other blocks (dental workpieces 2) of polygonal cross-section (see FIGS. 14a through 17c).

The holding element 3 preferably comprises PMMA and the fixing device POM. In principle, however, it is also possible to use any other materials which are also suitable for fulfilling the function involved. Thus, the holding element 3 can be made, for example, from a high-grade steel and the fixing device 4 from aluminum. Preferably, the material of the fixing device 4 is always softer and thus more easily deformable than the holding element 3.

In relation to FIG. 18a, it should once again be explained that the necessary components of the invention can be made available to a customer in the form of a holding apparatus 1. However, the holding element 3 and the fixing device 4 can be supplied to the customer as a pure blank, that is to say without conical surfaces, milled-out noses and so forth. If the customer should already be in possession of a processing machine 13 of the present applicant, it is then possible for the customer to clamp those blank blocks in the processing machine 13 and to independently produce the parts according to the invention of the holding apparatus 1. For that purpose, the customer then only has to buy in the data carrier 17 with the data N (CNC files) and the blank blocks or to enable the holding apparatus production mode $P_1$ already stored in the processing machine 13, by the input of a code which is to be purchased.

Both embodiments show a holding apparatus 1 with which workpieces 2 (zirconium blocks) can be clamped fast in force-locking relationship. In that respect, the illustrated options are of such a design configuration that the clamping force is applied to a large part of the peripheral surface (peripheral surface U). The basic idea is that the blocks (workpieces 2) are firstly inserted into the holding apparatus 1. By virtue of the fact that the latter is produced with a yielding structure, preferably of POM, and has a relatively narrow split sleeve, the holding apparatus 1 is correspondingly flexible and then also adapts to the blank (workpiece 2). That is also the case if the blank should be slightly larger than the opening 8 in the holding apparatus 1.

Especially in regard to the second embodiment (see FIGS. 9a through 13b), it is to be stressed that the clamping wedge member (fixing device 4 in the form of the clamp 24) can be inserted as soon as the workpieces 2 are fitted in place. In that respect, the clamping wedge has such a configuration that it conically converges on the top side and the underside (guide portion 25) so that it can be more easily pressed into place. The operation of pressing it in is effected here only by manual force. Depending on how wide the projecting projections are or how small the minimum spacing $A_H$ is, the clamping force is higher or lower. The correspondingly wider that they are, then the correspondingly higher is also the clamping force exerted on the blank. With this variant, care should be taken to ensure that two workpieces 2 are always clamped in mutually opposite relationship as otherwise the clamping mechanism is too unstable. If there should be a wish to clamp only one workpiece 2, then a "blind plug" should be inserted on the other side. The clamping wedge is preferably made from PMMA as that material has good sliding capabilities. In general, it is to be stated in this respect that other materials which achieve the aim of fixing can also be used for each part. The illustrated configuration affords space for six blanks, in which respect there can also be more or fewer. The number is then limited upwardly only by the amount of space required.

In the further variant (FIGS. 14a through 17c) of the second embodiment, the blank no longer has a round shape, but instead has a substantially cuboidal shape. It can be seen that the clamping mechanism is based on the same principle as the first variant of the second embodiment. In this case, a fixed guide/abutment for the blank is provided on the lower side of the holding element 3, that faces away from the slit 5. The clamping force is then again applied on the upper side by the clamping wedge member (clamp 24). In that case, the clamp surfaces H of the clamping wedge member have substantially the same geometry as in the first variant. Naturally, that also relates to those significant and functional regions of the wedge member. In this variant also the block, preferably the zirconium block, is again fitted into the clamping block (holding element 3) and then the clamping wedge member is pushed in by manual force.

Both variants of the second embodiment are designed so that the blank is gripped over a large surface area and so that "peripheral embrace" is interrupted only at one location (slit 5). Precisely that location is such that the clamping wedge member tries to reduce the open location in the peripheral embrace so that a peripheral force is exerted on the blank. A further advantage here is that the wedge member does not come directly into contact with the blank and no tools are required for the clamping effect. That system is thus highly user-friendly.

In the ideal case, the blanks (workpieces 2) have the same height as the clamping mechanism (holding apparatus 1) so that in use, all components can simply be placed on a table and all pushed together. If the blanks are to be lower or higher, a spacer disc can be placed therebeneath to permit a central position for the blank in the clamping block.

The entire set 12 can then be gripped in a milling system (processing machine 13). Depending on whether individual working operations or multi-component dental operations are to be carried out, it is possible to choose between the different variants.

LIST OF REFERENCES 1 holding apparatus (clamping block or clamping mechanism)
2 workpiece (blank)
3 holding element (holding frame or carrier plate)
4 fixing device (clamping wedge member)
5 slit
6 guide
7 nose
8 opening
9 groove 10 tool
11 connecting elements
12 set
13 processing machine
14 processing tool
15 positioning device
16 memory
17 data carrier
18 clamping surfaces
19 counterpart connecting portions
20 recesses
21 open-loop or closed-loop control unit
22 fixing means
23 holding ring
24 clamp
25 guide portion
26 bow portion
27 opening
R relative movement
$K_3$ guide or wedge surface on the holding element
$K_4$ guide or wedge surface on the fixing device
L longitudinal axis
M clamping surface
$Z_1$ loose condition
$Z_2$ wedged condition
D diameter of the clamping surface
$D_1$ inside diameter in the loose condition
$D_2$ inside diameter in the wedged condition
F guide surface
Q transverse plane
α angle of the guide surface
β angle of the guide or wedge surfaces
B wide side
S narrow side
$D_B$ maximum diameter wide side
$D_S$ maximum diameter narrow side
$P_1$ holding apparatus production mode
$P_2$ dental workpiece production mode
N data
U peripheral surface
H clamp surfaces
G counterpart clamp surfaces
$A_H$ minimum spacing of the clamp surfaces
$A_G$ spacing of the counterpart clamp surfaces

The invention claimed is:

1. A holding apparatus for holding a workpiece, comprising:
   a holding element; and
   a fixing device, said holding element and said fixing device being configured to hold the workpiece due to a movement of said fixing device relative to said holding element;
   wherein one of said fixing device or said holding element comprises a split sleeve having a slit extending an entire axial length of said one of said fixing device or said holding element; and
   wherein said holding element and said fixing device have corresponding wedge surfaces, at least one of said corresponding wedge surfaces being inclined relative to a longitudinal axis of said split sleeve, said corresponding wedge surfaces being formed such that, upon the movement of said fixing device relative to said holding element along the longitudinal axis of said split sleeve, said corresponding wedge surfaces bear against each other to fix said fixing device against said holding element by wedging; and
   wherein an inside surface of said split sleeve forms a clamping surface for holding the workpiece such that, upon the movement of said fixing device relative to said holding element along the longitudinal axis of said split sleeve, the workpiece is held by said clamping surface.

2. The holding apparatus as set forth in claim 1, wherein said split sleeve has a part-annular configuration around a longitudinal axis.

3. The holding apparatus as set forth in claim 1, wherein said clamping surface of said split sleeve is configured to have a first inside diameter corresponding to a loose condition of said split sleeve, and to have a second inside diameter corresponding to a braced condition of said split sleeve due to the movement of said fixing device relative to said holding element, said second inside diameter being less than said first inside diameter due to a narrowing of said slit.

4. The holding apparatus as set forth in claim 1, wherein said fixing device comprises said split sleeve provided separately from said holding element.

5. The holding apparatus as set forth in claim 4, wherein said wedge surface of said fixing device is formed by an at least partially conical outside surface of said fixing device.

6. The holding apparatus as set forth in claim 1, wherein said holding element comprises said split sleeve and has a one-piece configuration with said split sleeve.

7. A holding apparatus for holding a workpiece, comprising:
   a holding element; and
   a fixing device, said holding element and said fixing device being configured to hold the workpiece due to a movement of said fixing device relative to said holding element;
   wherein one of said fixing device or said holding element comprises a split sleeve having a slit extending an entire axial length of said one of said fixing device or said holding element, an inside surface of said split sleeve forming a clamping surface for holding the workpiece such that, upon the movement of said fixing device relative to said holding element, the workpiece is held by said clamping surface;
   wherein said holding element and said fixing device have corresponding wedge surfaces, at least one of said corresponding wedge surfaces being inclined relative to a longitudinal axis of said split sleeve, said corresponding wedge surfaces being formed such that, upon the movement of said fixing device relative to said holding element, said corresponding wedge surfaces bear against each other to fix said fixing device against said holding element by wedging;
   wherein said holding element comprises said split sleeve and has a one-piece configuration with said split sleeve; and
   wherein said fixing device has a clamp having two spaced apart clamp surfaces forming said wedge surface of said fixing device, said clamp surfaces being configured to be applied against spaced apart counterpart clamp surfaces in a region of said slit and facing away from said clamping surface, said counterpart clamp surfaces forming said wedge surface of said holding element.

8. The holding apparatus as set forth in claim 1, wherein said holding element has a pair of curved portions for holding the workpiece therebetween, said pair of curved portions being separated by said slit, said holding element and said fixing device being configured such that said corresponding wedge surfaces bearing against each other upon the movement of said fixing device relative to said holding element press said pair of curved portions together to thereby hold the workpiece.

9. A set comprising:
said holding apparatus as set forth in claim 1; and
a dental workpiece having a circular cylindrical shape.

10. A processing machine comprising:
a processing tool; and
said holding apparatus as set forth in claim 1.

11. The processing machine as set forth in claim 10, wherein the processing machine is a CNC machine.

12. The processing machine as set forth in claim 10, further comprising a moveable positioning device having a cardan joint configuration, said holding apparatus being releasably fixed to said positioning device.

13. A holding apparatus for holding a workpiece, comprising:
a holding element; and
a fixing device, said holding element and said fixing device being configured to hold the workpiece due to a movement of said fixing device relative to said holding element;
wherein one of said fixing device or said holding element comprises a split sleeve having a slit extending an entire axial length of said one of said fixing device or said holding element, an inside surface of said split sleeve forming a clamping surface for holding the workpiece such that, upon the movement of said fixing device relative to said holding element, the workpiece is held by said clamping surface; and
wherein said holding element and said fixing device have corresponding wedge surfaces, at least one of said corresponding wedge surfaces being flat and inclined relative to a longitudinal axis of said split sleeve, the longitudinal axis extending along an axial length of said one of said fixing device or said holding element, said corresponding wedge surfaces being formed such that, upon the movement of said fixing device relative to said holding element along the longitudinal axis, said corresponding wedge surfaces bear against each other to fix said fixing device against said holding element by wedging.

* * * * *